United States Patent
Chen et al.

(10) Patent No.: US 12,220,440 B2
(45) Date of Patent: Feb. 11, 2025

(54) DRUG COMPOSITION, METHOD FOR TREATING INFECTION, DISINFECTING COMPOSITION, AND DRUG ADJUVANT

(71) Applicant: City University of Hong Kong, Kowloon (HK)

(72) Inventors: Sheng Chen, Kowloon (HK); Chen Xu, Kowloon (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 17/862,617

(22) Filed: Jul. 12, 2022

(65) Prior Publication Data
US 2024/0016883 A1    Jan. 18, 2024

(51) Int. Cl.
| | | |
|---|---|---|
| *A61K 38/12* | (2006.01) | |
| *A01N 37/46* | (2006.01) | |
| *A01N 63/50* | (2020.01) | |
| *A01P 1/00* | (2006.01) | |
| *A61K 31/245* | (2006.01) | |
| *A61P 31/04* | (2006.01) | |

(52) U.S. Cl.
CPC .............. *A61K 38/12* (2013.01); *A01N 37/46* (2013.01); *A01N 63/50* (2020.01); *A01P 1/00* (2021.08); *A61K 31/245* (2013.01); *A61P 31/04* (2018.01)

(58) Field of Classification Search
None
See application file for complete search history.

(56) References Cited

PUBLICATIONS

Xu et al. "Otilonium bromide boosts antimicrobial activities of colistin against Gram-negative pathogens and their persisters" Communications Biology 5:613. (Year: 2022).*
Zhou et al. "Repurposing Antispasmodic Agent Otilonium Bromide for Treatment of Staphylococcus aureus infections" Frontiers in Microbiology 11:1720. (Year: 2020).*
Tsubery et al. "Modulation of the Hydrophobic Domain of Polymyxin B Nonapeptide: Effect on Outer-Membrane Permeabilization and Lipopoylsaccharide Neutralization" Molecular Pharmacology 62:1036-1024. (Year: 2002).*
Nature Microbiology | vol. 5 |Aug. 2020 | 1040-1050 | www.nature.com/naturemicrobiology | A broad-spectrum antibiotic adjuvant reverses multidrug-resistant Gram-negative pathogens M. Song et al.
To cite this article: Alankar Shrivastava & Ashu Mittal (2022) A Mini Review on Characteristics and Analytical Methods of Otilonium Bromide, Critical Reviews in Analytical Chemistry, 52:7, 1717-1725, DOI: 10.1080/10408347.2021.1913983.
Frontiers in Microbiology | www.frontiersin.org | Jun. 2017 | vol. 8 | Article 1104 | published: Jun. 16, 2017 doi: 10.3389/fmicb.2017.

01104 A Novel Approach for Combating Klebsiella pneumoniae Biofilm Using Histidine Functionalized Silver Nanoparticles; S. Chhibber et al.
Biochimica et Biophysica Acta 859 (1986) 125-134 Elsevier; Action of calcium channel and beta-adrenergic blocking agents in bilayer lipid membranes; B. Shi et al.
Frontiers in Microbiology | www.frontiersin.org | Aug. 2019 | vol. 10 | Article 1847 | AmrZ Regulates Swarming Motility Through Cyclic di-GMP-Dependent Motility Inhibition and Controlling Pel Polysaccharide Production in Pseudomonas aeruginosa PA14 | L. Hou et al.
J. Med. Chem. 2019, 62, 8665-8681 | pubs.acs.org/jmc | DOI: 10.1021/acs.jmedchem.8b01781J. Med. Chem. 2019, 62, 8665-8681 | Antibiotic Adjuvants: Make Antibiotics Great Again! | H. Douafer et al.
Cell 172, Feb. 22, 2018 © 2018 Elsevier Inc. DOI http://dx.doi.org/10.1016/j.cell.2018.02.018 | SnapShot: Antibiotic Resistance | I. Yelin et al.
Nature Microbiology | www.nature.com/naturemicrobiology | Bacterial metabolic state more accurately predicts antibiotic lethality than growth rate | A. Lopatkin et al.
Nature Communications | DOI: 10.1038/s41467-017-02149-0 | Balancing mcr-1 expression and bacterial survival is a delicate equilibrium between essential cellular defence mechanisms | Q. Yang et al.
www.thelancet.com/infection vol. 16 Mar. 2016 | Carbapenem-resistant and colistin-resistant *Escherichia coli* co-producing NDM-9 and MCR-1.
Biochimica et Biophysica Acta 1807 (2011) 1507-1538 | Chemiosmotic coupling in oxidative and photosynthetic phosphorylation | P. Mitchell.
ISSN: 1478-7210 (Print) 1744-8336 (Online) Journal homepage: http://www.tandfonline.com/loi/ierz20 | Colistin: an update on the antibiotic of the 21st century | S. Biswas et al.
ISSN: (Print) (Online) Journal homepage: https://www.tandfonline.com/loi/temi20 | Emerging Microbes & Infections | Colistin and its role in the Era of antibiotic resistance: an extended review (2000-2019) | M. Ahmed et al.
Sabnis et al. eLife 2021; 10:e65836. DOI: https://doi.org/10.7554/eLife.65836 | Colistin kills bacteria by targeting ipopolysaccharide in the cytoplasmic membrane.
www.thelancet.com/infection vol. 16 Mar. 2016 | Colistin resistance gene mcr-1 in extended spectrum β-lactamase producing and carbapenemase producing Gram-negative bacteria in Germany.
www.thelancet.com/infection vol. 16 Mar. 2016 | Colistin-resistant *Escherichia coli* harbouring mcr-1 isolated from food animals in Hanoi, Vietnam.
Apr. 7, 2011 DOI: 10.1016/S1473-3099(11)70059-7 | www.thelancet.com/infection vol. 11 May 2011 | Dissemination of NDM-1 positive bacteria in the New Delhi environment and its implications for human health: an environmental point prevalence study | T. Walsh et al.
www.thelancet.com/infection vol. 16 Feb. 2016 | Dec. 17, 2015 http://dx.doi.org/10.1016/S1473-3099(1540-X Abiola Olumuyiwa Olaitan, Selma Chabou, Liliane Okdah, Serge Morand, | Jean-Marc Rolain.

(Continued)

*Primary Examiner* — Sudhakar Katakam
*Assistant Examiner* — Zachary J Miknis
(74) *Attorney, Agent, or Firm* — Renner, Kenner, Greive, Bobak, Taylor & Weber

(57) ABSTRACT

A drug composition contains an effective amount of a drug active containing a polymyxin, an effective amount of otilonium bromide, and a pharmaceutically-acceptable carrier. A method for treating or protecting against a Gram-negative infection containing the step of administering a drug composition, a disinfecting composition similar to the drug composition, and an adjuvant for a drug active also may contain otilonium bromide.

1 Claim, 9 Drawing Sheets

(56) References Cited

PUBLICATIONS

Nature Publishing Group vol. 451|Jan. 24, 2008| doi: 10.1038/nature06449 | Distinct roles of the FliI ATPase and proton motive force in bacterial flagellar protein export | T. Minamino et al.

Nature Reviews | Microbiology | https://doi.org/10.1038/s41579-018-0141-x |Drug combinations: a strategy to extend the life of antibiotics in the 21st century | M. Tyers et al.

J Antimicrob Chemother 2018; 73: 1862-1871 doi:10.1093/jac/dky134 Advance Access publication Apr. 26, 2018 | Efflux pump inhibitor CCCP to rescue colistin susceptibility in mcr-1plasmid-mediated colistin-resistant strains and Gram-negative bacteria | S. Baron et al.

Emergence of plasmid-mediated colistin resistance mechanism MCR-1 in animals and human beings in China: a microbiological and molecular biological study |Lancet Infect Dis 2016;16: 161-68 | Y. Liu et al.

Exploring the Antimicrobial Action of Quaternary Amines against Acinetobacter baumannii | G. Knauf et al | American Society for Microbiology | Jan./Feb. 2018 vol. 9 Issue 1 e02394-17.

Genetic Features of MCR-1-Producing Colistin-Resistant *Escherichia coli* Isolates in South Africa | L. Poirel et al | American Society | aac.asm.org Antimicrobial Agents and Chemotherapy Jul. 2016 vol. 60 No. 7.

Genomic Epidemiology of Complex, Multispecies, Plasmid-Borne blaKPC Carbapenemase in Enterobacterales in the United Kingdom from 2009 to 2014 | N. Stoesser et al | May 2020 vol. 64 Issue 5 e02244-19 Antimicrobial Agents and Chemotherapy aac.asm.org.

Adv. Therap. 2020, 3, 2000084 | DOI: 10.1002/adtp.202000084 | Imidazole Type Antifungal Drugs Are Effective Colistin Adjuvants That Resensitize Colistin-Resistant Enterobacteriaceae | C. Xu et al.

FEMS Microbiol Lett 281 (2008) 81-86 | DOI:10.1111/j.1574-6968.2008.01089.x | Inhibition of swarming motility of Pseudomonas aeruginosa by branched-chainfattyacids | T. Inoue et al.

Large Nosocomial Outbreak of Colistin-Resistant, Carbapenemase-Producing Klebsiella pneumoniae Traced to Clonal Expansion of an mgrB Deletion Mutant | Oct. 2015 vol. 53 No. 10 Journal of Clinical Microbiology jcm.asm.org | T. Giani et al.

Annu. Rev. Biochem. 2002. 71:635-700 DOI: 10.1146/annurev.biochem.71.110601.135414 | Lipopolysaccharide Endotoxins | C. Raetz et al.

Dovepress http://dx.doi.org/10.2147/CEG.S46291 | Long-term efficacy and safety of otilonium bromide in the management of irritable bowel syndrome: a literature review | J. Triantafillidis et al.

Adv. Sci. 2020, 7, 1902227 | DOI: 10.1002/advs.201902227 | Metformin Restores Tetracyclines Susceptibility against Multidrug Resistant Bacteria | Y. Liu et al.

Frontiers in Microbiology | www.frontiersin.org | Aug. 2018 | vol. 9 | Article 1724 | Novel Glycopolymer Eradicates Antibiotic- and CCCP-Induced Persister Cells in Pseudomonas aeruginosa | V. Narayanaswamy et al.

aac.asm.org Antimicrobial Agents and Chemotherapy Apr. 2016 vol. 60 No. 4 | Occurrence of the Plasmid-Borne mcr-1 Colistin Resistance Gene in Extended-Spectrum-β-Lactamase-Producing Enterobacteriaceae in River Water and Imported Vegetable Samples in Switzerland | K. Zurfuh et al.

Antimicrobial Agents and Chemotherapy, Sep. 2010, p. 3770-3775 vol. 54, No. 9 0066-4804/10/$12.00 doi:10.1128/AAC.00620-10 | Optimized Nile Red Efflux Assay of AcrAB-ToIC Multidrug Efflux System Shows Competition between Substrates | J. Bohnert e t al.

Current Pharmaceutical Design, 2018, 24, 1772-1779 | Otilonium Bromide: A Drug with a Complex Mechanism of Action |S. Evangelista et al.

Communications Biology | (2022) 5:613 | https://doi.org/10.1038/s42003-022-03561-z | www.nature.com/commsbio | Otilonium bromide boosts antimicrobial activities of colistin against Gram-negative pathogens and their persisters | C. Xu et al.

Performance Standards for Antimicrobial Susceptibility Testing | Clinical and Laboratory Standards Institute | M100, 28th ed. Jan. 2018 Replaces M100, 27th ed. | M. Weinstein et al.

Adv. Sci. 2021, 8, 2100749 | DOI: 10.1002/advs.202100749 | Plant Natural Flavonoids Against Multidrug Resistant Pathogens | M. Song et al.

www.thelancet.com/infection vol. 16 Mar. 2016 | Plasmid-mediated carbapenem and colistin resistance in a clinical isolate of *Escherichia coli*.

Cold Spring Harb Perspect Med 2016;6:a025288 | Polymyxin: Alternative Mechanisms of Action and Resistance | M. Trimble et al.

American Society for Microbiology | Apr. 2017 vol. 30 Issue 2 Clinical Microbiology Reviews cmr.asm.org 557 | Polymyxins: Antibacterial Activity, Susceptibility Testing, and Resistance Mechanisms Encoded by Plasmids or Chromosomes | L. Poirel et al.

Pharmacology and Therapeutics 181 (2018) 85-90 | http://dx.doi.org/10.1016/j.pharmthera.2017.07.012 | Polymyxins for CNS infections: Pharmacology and neurotoxicity | T. Velkov et al.

www.eurosurveillance.org | Rapid Communications | Prevalence of mcr-1 in commensal *Escherichia coli* from French livestock, 2007 to 2014 | A. Perrin-Guyomard et al.

www.pnas.org/cgi/doi/10.1073/pnas.1101130108 PNAS | Apr. 19, 2011 | vol. 108 | No. 16 | E77-E81 Microbiology PNAS Plus | Real-time attack on single *Escherichia coli* cells by the human antimicrobial peptide LL-37 | K. Sochacki et al.

J. Cell. Mol. Med. vol. 21, No. 4, 2017 pp. 735-745 | Repeated otilonium bromide administration prevents neurotransmitter changes in colon of rats underwent to wrap restraint stress | C. Traini et al.

Frontiers in Microbiology | www.frontiersin.org | Jul. 2020 | vol. 11 | Article 1720 | Repurposing Antispasmodic Agent Otilonium Bromide for Treatment of *Staphylococcus aureus* Infections | L. Zhou et al.

Antimicrobial Agents and Chemotherapy, Sep. 2009, p. 3628-3634 vol. 53, No. 9 doi:10.1128/AAC.00284-09 | Resistance to Colistin in Acinetobacter baumannii Associated with Mutations in the PmrAB Two-Component System | M. Adams et al.

Pharmacotherapy vol. 30, No. 12, 2010 | Resurgence of Colistin: A Review of Resistance, Toxicity, Pharmacodynamics, and Dosing | L. Lim et al.

www.nature.com/scientificreports (2019) 9:19990 | https://doi.org/10.1038/s41598-019-56299-w | Reversibility of membrane permeabilization upon pulsed electric field treatment in Lactobacillus plantarum WCFS1 | E. Vaessen et al.

Nature Nanotechnology | www.nature.com/naturenanotechnology | Role of bacterial motility in differential resistance mechanisms of silver nanoparticles and silver ions | L. Stabryla et al.

Journal of Medical Microbiology (2011), 60, 699-709 DOI 10.1099/jmm.0.030932-0 | Role of persister cells in chronic infections: clinical relevance and perspectives on anti-persister therapies | M. Fauvart et al.

Journal of Bacteriology, Sep. 2009, p. 5592-5602 vol. 191, No. 18 0021-9193/09/$08.000 doi:10.1128/JB.00157-09 | Swarming of Pseudomonas aeruginosa Is Controlled by a Broad Spectrum of Transcriptional Regulators, Including MetR | A. Yeung et al.

Tackling Drug-Resistant Infections Globally: Final Report and Recommendations the Review on Antimicrobial Resistance Chaired by Jim O'Neill May 2016.

Li X-Z, Plésiat P, Nikaido H. Mar. 18, 2015. The challenge of effluxmediated antibiotic resistance in Gram-negative bacteria. Clin Microbiol Rev doi:10.1128/CMR.00117-14.

ISSN: 2150-5594 (Print) 2150-5608 (Online) Journal homepage: https://www.tandfonline.com/loi/kvir20 | The global epidemiology of carbapenemase producing Enterobacteriaceae | D. Duin et al.

Trends in Microbiology, Sep. 2018, vol. 26, No. 9 https://doi.org/10.1016/j.tim.2018.02.006 | Towards UnderstandingMCR-likeColistin Resistance | J. Sun et al.

Am J Physiol Gastrointest Liver Physiol 298: G706-G713, 2010. First published Mar. 4, 2010; doi: 10.1152/ajpgi.00437.2009. | T-type Ca2 channel modulation by otilonium bromide | P. Strege et al.

Biochimica et Biophysica Acta 1758 (2006) 1587-1595 | www.sciencedirect.com | Verapamil, a Ca2+ channel inhibitor acts as a local anesthetic and induces the sigma E dependent extracytoplasmic stress response in *E. coli* | C. L. Andersen et al.

(56) References Cited

PUBLICATIONS

International Journal of Antimicrobial Agents 42 (2013) 379-383 | What do we know about resistance to colistin in Enterobacteriaceaein avian and pig production in Europe? | I. Kempf et al.

\* cited by examiner (b)

(c)

(d)

US 12,220,440 B2

DRUG COMPOSITION, METHOD FOR TREATING INFECTION, DISINFECTING COMPOSITION, AND DRUG ADJUVANT

FIELD OF THE INVENTION

The present invention relates to an adjuvant for a pharmaceutical composition. More specifically, the present invention relates to an adjuvant for a pharmaceutical composition for multi-drug-resistant bacteria. Even more specifically, the present invention relates to an adjuvant for a pharmaceutical composition for Gram-negative multi-drug-resistant bacteria.

BACKGROUND

Colistin (a.k.a., polymyxin E) is a well-known antibiotic discovered in 1947 and is currently-used as a last-resort for treating multi-drug-resistant (MDR) Gram-negative bacteria, including *Psuudomonas aeruginosa, Klebsiella pneumoniae, Acinobacter*, etc. Colistimethate sodium is typically administered via injection as a prodrug with reduce toxicity while colistin sulfate is administered orally or topically and absorbed into the skin. Colistin is on the WHO's list of Essential Medicines and it is categorized as a critically important human medicine. However, colistin has a known toxicity and thus its use is carefully controlled.

However, all bacterial populations, including those of non-antibiotic resistant strains, are known to harbor a certain drug tolerant sub-population that does not respond to antimicrobial actions of antibiotics. Since about 2015, the emergence and widespread dissemination of colistin-resistant Gram-negative pathogens, as well as the cytotoxicity of colistin itself, severely limit the application of colistin in clinical settings for infection treatment of multidrug resistant organisms. However, the development of new drugs and their approval process is both long and full of false starts, as many promising drugs ultimately possess unacceptable side effects.

To combat bacterial colistin resistance several colistin adjuvants have been discovered including antimicrobial compounds, FDA approved drugs, Eukaryotic kinase inhibitors, cationic block beta-peptide, and small molecular compounds. These compounds exhibit different effect levels with colistin and may potentate its activity against colistin-resistant enterobacteriaceae (CAE). However, most of these published compounds either lack in vivo efficacy data or mechanistic understanding of their action, hence further development of these compounds for clinical use is difficult or prohibited.

Although previous studies recommended otilonium bromide in the oral treatment of irritable bowel syndrome by using it as a calcium channel blocker, its potential in treating bacterial infections has not been extensively studied Accordingly the need exists for more effective compositions for treatments for MDR bacteria, and especially MDR Gram-negative bacteria. The need exists for a drug which maintains colistin's efficacy with reduced toxicity and/or side effects. The need also exists to identify an action mechanism for colistin adjuvants.

SUMMARY OF THE INVENTION

An embodiment of the present invention relates to a drug composition containing an effective amount of a drug active containing a polymyxin, an effective amount of otilonium bromide, and a pharmaceutically-acceptable carrier.

An embodiment of the present invention relates to a method for treating or protecting against a Gram-negative infection containing the step of administering a drug composition containing an effective amount of a drug active comprising a polymyxin, an effective amount of otilonium bromide, and a pharmaceutically-acceptable carrier.

An embodiment of the present invention relates to a disinfecting composition containing an effective amount of a drug active containing a polymyxin, an effective amount of otilonium bromide, and a pharmaceutically-acceptable carrier.

An embodiment of the present invention relates to an adjuvant for a drug active comprising an effective amount of otilonium bromide.

Without intending to be limited by theory, it is believed that otilonium bromide may re-sensitize Gram-negative bacteria to a polymyxin; especially colistin, colistimethate sodium, colistin sulfate, polymyxin B, and a combination thereof. Accordingly, when a Gram-negative polymyxin-resistant bacteria; or a MDR Gram-negative bacteria is resistant to a polymyxin, it is believed that treating the Gram-negative polymyxin-resistant bacteria with otilonium bromide may re-sensitize the bacteria to the polymyxin. It is also believed that reducing bacterial resistance to a polymyxin may also allow improved infection treatment while simultaneously reducing drug concentrations, thereby reducing potential side effects as well. It is therefore believed that the drug compositions, methods of treatment, uses, disinfecting compositions, and adjuvant herein may reduce and/or reverse the resistance of polymyxin-persistent bacteria.

BRIEF DESCRIPTION OF THE DRAWINGS

FIG. 6b shows a graph of the migration distance in FIG. 6a; and

Figure 1A:
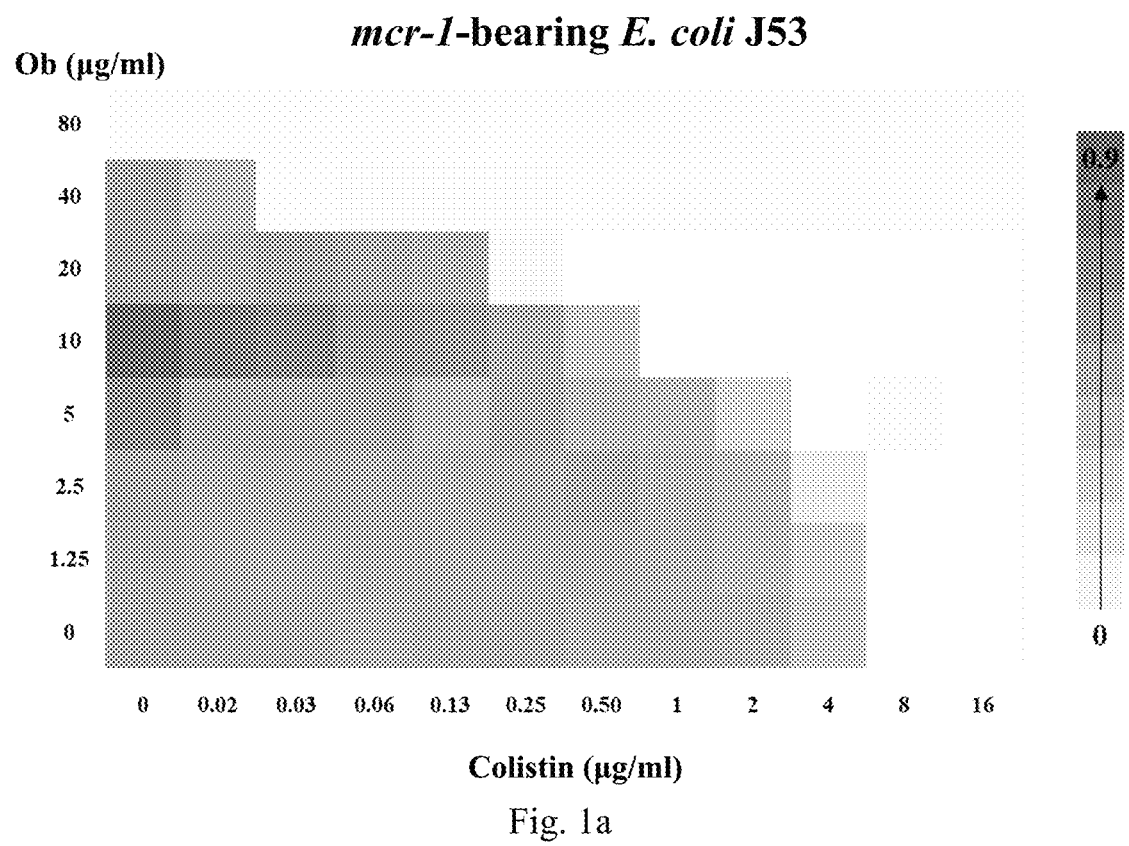
FIG. 1a shows a MIC checkerboard dilution assay of an embodiment of the invention in mcr-1 bearing *E. coli* J53.

The figures herein are for illustrative purposes only and are not necessarily drawn to scale.

DESCRIPTION OF THE PREFERRED EMBODIMENTS

Unless otherwise specifically provided, all tests herein are conducted at standard conditions which include a room and testing temperature of 25° C., sea level (1 atm.) pressure, pH 7, and all measurements are made in metric units. Furthermore, all percentages, ratios, etc. herein are by weight, unless specifically indicated otherwise. It is understood that unless otherwise specifically noted, the materials compounds, chemicals, etc. described herein are typically commodity items and/or industry-standard items available from a variety of suppliers worldwide.

As used herein the dosage for an "adult" is based on a 65 kg human, whereas the dosage for a "child" is based on a 32.5 kg human.

An embodiment of the present invention relates to a drug composition containing an effective amount of a drug active targeting a bacterial cell membrane such as a polymyxin, an effective amount of otilonium bromide, and a pharmaceutically-acceptable carrier.

Without intending to be limited by theory, it is believed that when a bacteria, especially a gram-negative bacteria, is resistant to a drug active, such as an antibiotic; or a drug active which targets a bacterial cell membrane; or a polymyxin; or the drug active is selected from the group of colistin, colistimethate sodium, colistin sulfate, polymyxin B, and a combination thereof, then a (USA) FDA-approved drug, specifically otilonium bromide may synergistically enhance the antimicrobial activity of a drug active as described herein. Accordingly, in an embodiment herein, the drug active is a polymyxin; or the drug active is selected from the group of colistin, colistimethate sodium, colistin sulfate, polymyxin B, and a combination thereof.

It has surprisingly been found that in bacteria which are resistant to the drug active, the combination of, for example, otilonium bromide and a polymyxin, may overcome the drug resistance and restore the sensitivity of the bacteria against the drug active. Specifically, the present invention identifies otilonium bromide as a non-toxic adjuvant that can restore the activity of colistin against colistin-resistant Gram-negative bacteria both in vitro and in an in vivo mouse infection model. It is believed that the adjuvant may also act synergistically with colistin to eradicate multidrug-tolerant persisters of Gram-negative bacteria in vitro. Functional studies and microcopy assays confirm that the synergistic antimicrobial effect of the otilonium bromide and colistin combination involves permeabilizing the Gram-negative bacterial cell membrane, dissipating proton motive force and suppressing efflux pumps, thereby damaging the membrane. This in turn may cause cytosol leakage and eventually bacterial cell death. Furthermore, otilonium bromide is believed to act as a strong membrane potential dissipater, without involving the mcr-1 gene product, causing a proton motive force (PMF) dissipation rate much higher than that of, for example, valinomycin a known PMF dissipater. Accordingly, it is believed that otilonium bromide as an adjuvant for a drug active herein can restore the clinical value of colistin in combating life-threatening Gram-negative pathogens and their persisters.

Without intending to be limited by theory, it is believed that colistin binds with the phosphate group of lipid A in lipopolysaccharide on the surface of Gram-negative bacterial membrane. Since lipid A acts as a hydrophobic anchor stabilizing bacteria's outer membrane structure, it is believed that divalent ions (e.g. $Ca^{2+}$ and $Mg^{2+}$) bind to a lipopolysaccharide to strengthen the bacterial cell membrane. It is further believed that the electrostatic interaction between the drug active and lipid A releases divalent ions from the bacterial cell membrane thereby destabilizing it. This allows the drug active to insert its hydrophobic chain and fatty acid group into the lipopolysaccharide (LPS) and diffuses from the bacteria's outer membrane into the inner membrane. This in turn forms pores leading to the disruption of bacterial cell membrane, and eventually (bacterial) cell death.

In the present invention, it is believed that otilonium bromide synergistically-complements this method of action as the positive charge may also bind with the negatively charged bacterial surface, promoting the penetration of the drug active's long-chain alkyl into the membrane. It is believed that these mechanisms reinforce each other to disrupt the delicately-balanced packing of the cell membranes causing leakage and bacterial cell death, even in bacteria believed to be resistant to the drug active; or colistin. Although otilonium bromide by itself exhibits an unexpectedly weak antibacterial effect on various Gram-negative pathogens, it surprisingly exhibits a strong synergistic effect when used in combination with the drug active herein.

Accordingly, it is believed through a mechanistic study that otilonium bromide acts synergistically with the drug active herein, for example, colistin, to permeabilize the bacterial cell membrane, dissipate PMF, inhibit multidrug efflux pump function and/or suppress bacterial motility. The increased membrane permeability induced by the combination of, for example, otilonium bromide and colistin, allows for self-promoted uptake of the colistin molecule, enabling it to reach the cytoplasmic membrane and cause cell death. However, it is found that the action of otilonium bromide and colistin could both be suppressed by a high concentration of divalent ions (especially $Ca^+$ ions). This data suggests that they could each displace the membrane-stabilizing divalent ions, resulting in an increase in (uncontrolled) membrane permeability. Furthermore, otilonium bromide is an amphipathic compound that contains both a hydrophilic quaternary amine and a hydrophobic long carbon chain. It is believed that these dual functional groups enable it to partition into the phospholipid biolayer of membrane and cause the aforementioned membrane damage.

It is believed that the otilonium bromide may also provide allow the physician to reduce the drug active dosage; or colistin dosage, required for effective treatment of infections caused by MDR bacteria; or MDR colistin-resistant bacteria; or colistin-resistant bacteria, thereby reducing the toxicity of the drug regimen and/or reducing the severity or occurrence of unwanted side effects. In an embodiment herein, the drug composition is prepared in a pre-measured dosage where the effective amount of a drug active is from about 8 mg to about 27 g; or from about 13 mg to about 26 g; or from about 15 mg to about 22.8 g for a 65 kg adult for oral administration. In an embodiment herein, the drug composition is prepared in a pre-measured dosage where the effective amount of a drug active is from about 4 mg to about 13.5 g; or from about 6.5 mg to about 13 g; or from about 7.5 mg to about 11.4 g for a 32.5 kg child for oral administration.

In an embodiment herein, the drug composition is prepared in a pre-measured dosage where the effective amount of a drug active is from about 8 mg to about 2.4 g; or from about 13 mg to about 2.3 g; or from about 32.5 mg to about 1.63 g for a 65 kg adult for intramuscular injection. In an embodiment herein, the drug composition is prepared in a pre-measured dosage where the effective amount of a drug active is from about 4 mg to about 1.2 g; or from about 6.5 mg to about 1.1 g; or from about 16.25 mg to about 0.82 g for a 32.5 kg child for intramuscular injection.

Colistin has the structure of Formula I, below, and a molecular weight of 1,155.45 g/mol.

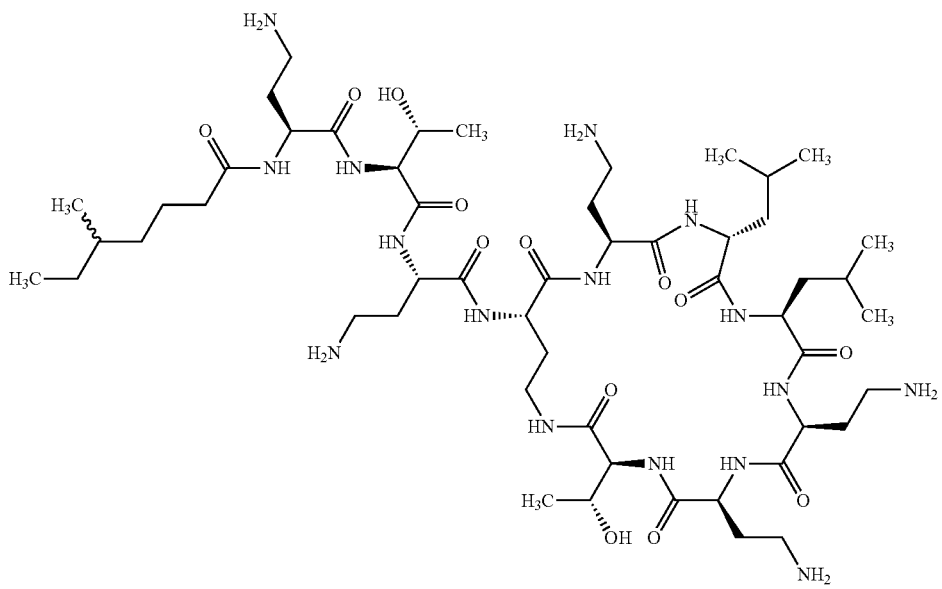

Formula I

Colistimethate sodium has the structure of Formula II and a molecular weight of 1750 g/mol.

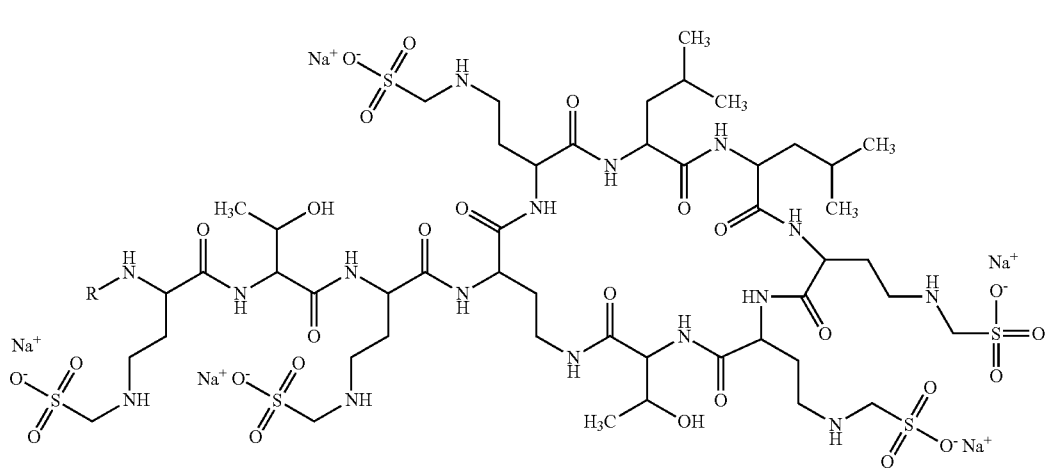

Formula II

Colistin sulfate has the structure of Formula III and a molecular weight of 28293 g/mol.

Formula III

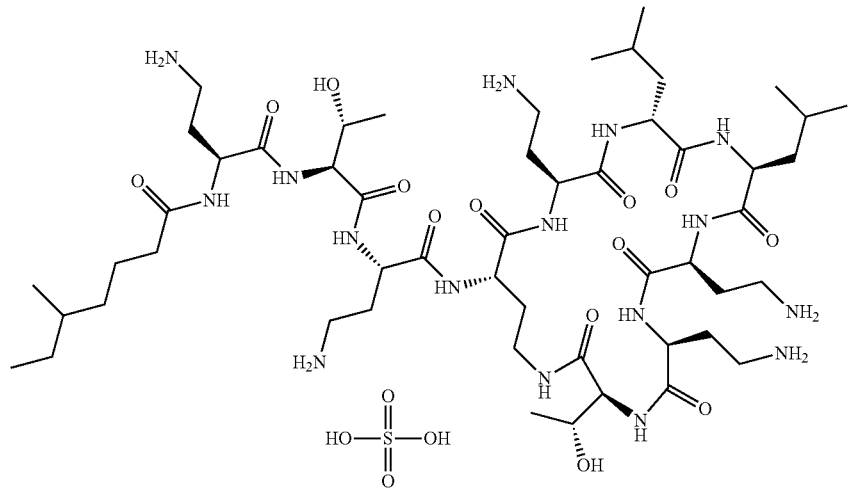

Polymyxin B has the structure of Formula III and a molecular weight of 1301.6 g/mol.

Formula IV

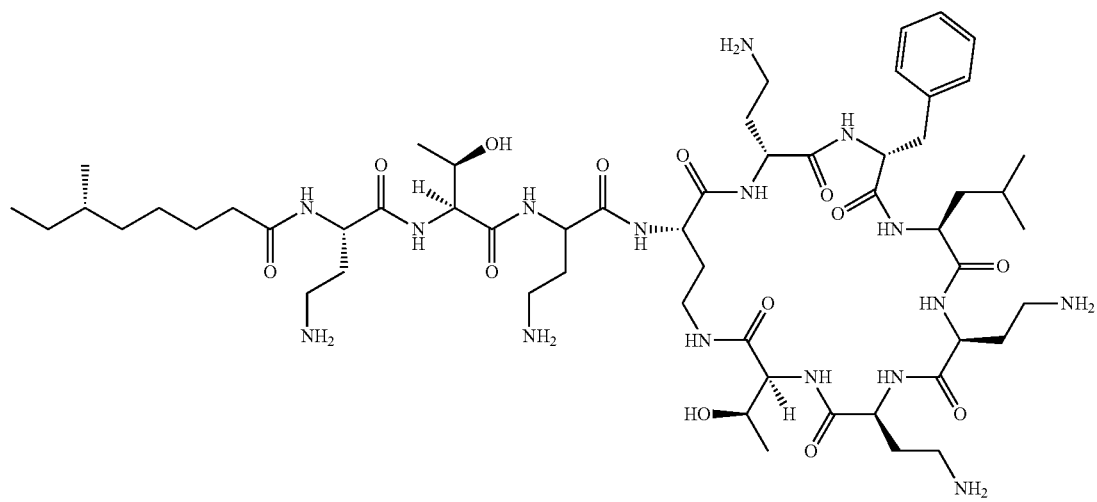

In an embodiment herein, the drug composition is prepared in a pre-measured dosage where the effective amount of otilonium bromide is from about 6.5 mg to about 39 g; or from about 13 mg to about 26 mg; or from about 32.5 mg to about 6.5 g for a 65 kg adult. In an embodiment herein, the drug composition is prepared in a pre-measured dosage where the effective amount of otilonium bromide is from about 3.3 mg to about 19.5 g; or from about 6.5 mg to about 13 g; or from about 16.2 mg to about 3.25 g for a 32.5 kg child. Such levels could be, for example, for oral or intramuscular administration.

Otilonium bromide has the structure of Formula V, below, and a mw of 563.57 g/mol.

Formula V

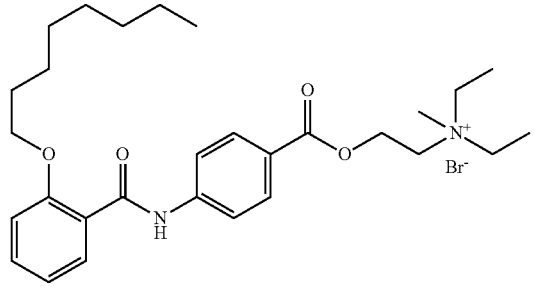

In an embodiment herein, the drug composition further contains a pharmaceutically-acceptable chelant therein. Without intending to be limited by theory, it is believed that a chelant may further provide a synergistic effect by helping to promote the removal of divalent ions from the bacterial cell membrane, by promoting the extraction of divalent ions from the membrane, and/or by capturing divalent ions in solution that would otherwise reintegrate back into the cell membrane so as to strengthen it. Such a chelant may be provided herein at a level consistent with existing levels in corresponding products and/or industry-standards.

Without intending to be limited by theory, it is believed that such a chelant may provide a synergistic effect to further bind free ions which could otherwise interfere with the membrane-disrupting activity of the drug active and/or the otilonium bromide.

In an embodiment herein, the drug composition may contain an additional drug ingredient such as another drug actives including another antibiotic, a preservative, a filler, etc. as known in the art, and at levels known in the art.

The drug composition herein may take on many different physical forms depending on, for example, the location and/or intensity of the infection to be treated. Thus, in an embodiment herein, the drug composition is in the form of an injection, a dilution preparation, a patch, a cream, a pill, a capsule, a powder, a liquid, and a combination thereof; or an injection, a patch, a cream, a pill, and a combination thereof, or a composition for oral administration or an injection; or an injection; or an intramuscular injection.

In an embodiment of the invention, the pharmaceutically-acceptable carrier is selected from the group consisting of water, saline solution, a buffer solution and a combination thereof; or water; or saline.

An embodiment of the invention herein relates to a method of treating or protecting against a Gram-negative infection including the step of administering a drug composition including an effective amount of a drug active containing a polymyxin; or where the drug active is selected from the group consisting of colistin, colistimethate sodium, colistin sulfate, polymyxin B, and a combination thereof, an effective amount of otilonium bromide, and a pharmaceutically-acceptable carrier.

An embodiment of the present invention further relates to the use of an effective amount of otilonium bromide, an effective amount of a drug active comprising a polymyxin, and a pharmaceutically-acceptable carrier in the manufacture of a medicament for the treatment or prophylaxis of a bacterial infection; or a Gram-negative infection; or a multi-drug-resistant bacterial infection.

An embodiment of the present invention also relates to the use of an effective amount of otilonium bromide, an effective amount of a drug active comprising a polymyxin, and a pharmaceutically-acceptable carrier in the treatment or prophylaxis of a bacterial infection; or a Gram-negative infection; or a multi-drug-resistant bacterial infection.

In an embodiment herein, the present invention also relates to the use of a drug composition for the treatment of prophylaxis of a Gram-negative bacterial infection, wherein the drug contains an effective amount of a drug active containing a polymyxin; or where the drug active is selected from the group consisting of colistin, colistimethate sodium, colistin sulfate, polymyxin B, and a combination thereof, an effective amount of otilonium bromide, and a pharmaceutically-acceptable carrier.

In an embodiment herein, the invention relates to the use of otilonium bromide in the manufacture of a drug composition for the treatment or prophylaxis of a Gram-negative bacterial infection. The drug composition may further contain an effective amount of a drug active selected from the group consisting of colistin, colistimethate sodium, colistin sulfate, polymyxin B, and a combination thereof, an effective amount of otilonium bromide, and a pharmaceutically-acceptable carrier.

In an embodiment herein, the Gram-negative infection is caused by a multi-drug-resistant bacteria; or a multi-drug-resistant bacteria resistant to the drug active herein; or a colistin-resistant multi-resistant bacteria, a polymyxin B-resistant multi-drug-resistant bacteria, and a combination thereof; or a colistin-resistant multi-resistant bacteria. In an embodiment herein, the multi-drug-resistant bacteria is selected from the group of *Pseudomonas, Acinetobacter, Escherichia, Salmonella*, and a combination thereof; or *A. baumannii, E. coli, P. aeruginosa, S. typhimurium*, and a combination thereof; or *A. baumannii, E. coli*, and a combination thereof; or *A. baumannii*; or *E. coli*; or *P. aeruginosa*; or *K. pneumoniae*; or *S. typhimurium*. In an embodiment herein, the bacteria; or Gram-negative bacteria; or multi-drug-resistant bacteria, possesses a bacterial cell membrane, and the invention herein disrupts the bacterial cell membrane.

In an embodiment of the drug and/or method herein, the effective amount of the drug active is from about 0.5 mg/kg to about 25 mg/kg; or from about 0.75 mg/kg to about 20 mg/kg; or from about 1 mg/kg to about 18 mg/kg, based on the weight of the subject; especially for oral administration. In an embodiment herein for intramuscular injection, the effective amount of the drug active is from about 0.125 mg/kg to about 38 mg/kg; or from about 0.2 mg/kg to about 35 mg/kg; or from about 0.5 mg/kg to about 25 mg/kg, based on the weight of the subject to be treated.

In an embodiment of the drug and/or method herein, the effective amount of otilonium bromide is from about 0.1 mg/kg to about 600 mg/kg; or from about 0.2 mg/kg to about 400 mg/kg; or from about 0.5 mg/kg to about 100 mg/kg or from about 1 mg/kg to about 50 mg/kg, based on the weight of the subject to be treated.

As noted herein, the drug composition may be in a variety of physical forms. Accordingly, the administration step may occur via a route selected from the group consisting of injection, oral administration, topical administration, and a combination thereof; or injection.

An embodiment of the invention herein also relates to a disinfecting composition containing an effective amount of a drug active containing a polymyxin; or wherein the drug active is selected from the group consisting of colistin, colistimethate sodium, colistin sulfate, polymyxin B, and a combination thereof, an effective amount of otilonium bromide, and a carrier. In such an embodiment where the disinfecting composition is intended to be used on, for example, surfaces such as hard surfaces, floors, operating tables, air vents, etc. the carrier need not be a pharmaceutically-acceptable carrier, and may contain ingredients which are not safe for human consumption or contact, but are instead intended to preserve or enhance the effectiveness of the disinfecting composition on such surfaces. Accordingly, the carrier useful herein for the disinfecting composition includes water, a filler, a disintegrant, and a combination thereof. The disinfecting composition herein may contain a chelant. The disinfecting composition may further contain other compounds found in disinfecting compositions such as, for example, ammonia, a bleach, a pH buffer, a perfume, a dye or colorant, and a combination thereof.

An embodiment of the present invention relates to an adjuvant for a drug active comprising an effective amount of otilonium bromide. Furthermore, the adjuvant herein may contain a drug active as described herein selected from the group of colistin, colistimethate sodium, colistin sulfate, polymyxin B, and a combination thereof.

EXAMPLE 1

Otilonium Bromide Potentiates Colistin Activity Against Both Colistin-Susceptible and Colistin-Resistant Bacteria In Vitro

*E. coli* J53 strain carrying a natural mcr-1-bearing IncI2 plasmid (33 kb, KX711706.1) is used to screen and identify colistin adjuvants which could enhance the antibacterial activity of colistin. FIG. 1a shows a MIC checkerboard dilution assay of an embodiment of the invention, otilonium bromide vs. colistin in mcr-1-bearing *E. coli* J53. Using the checkerboard dilution assay, otilonium bromide (Ob) is found to act synergistically with colistin (FICI=0.25), conferring a 32-fold reduction in colistin MIC (minimum inhibitory concentration), from 8 µg/ml to 0.28 µg/ml, when 20 µg/ml of otilonium bromide is used in the susceptibility test. The figure shows that the degree of reduction in MIC is sufficient to bring the MIC of the majority of the test strain to a level below the clinical breakpoint (2 µg/ml, according to CLSI 2020).

Figure 1B:
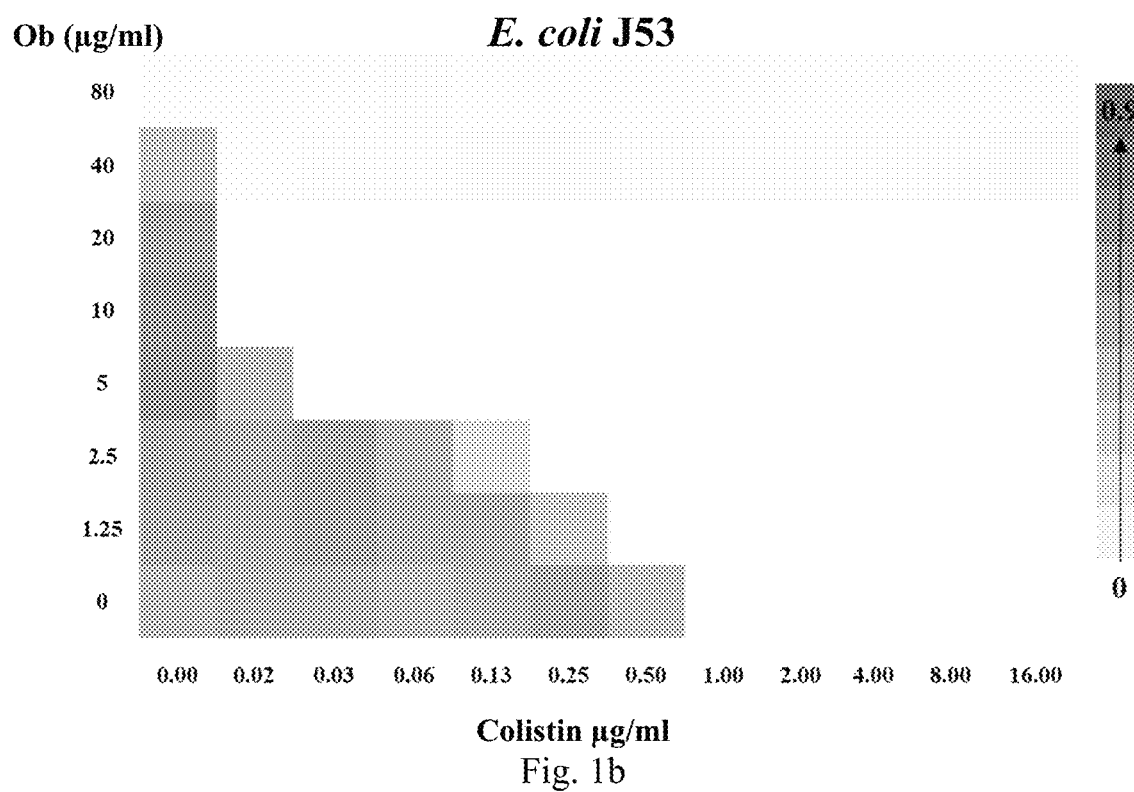
FIG. 1b shows a MIC checkerboard dilution assay of an embodiment of the invention in *E. coli* J53.

FIG. 1b shows a MIC checkerboard dilution assay of an embodiment of the invention, otilonium bromide cs. colistin in *E. coli* J53. Otilonium bromide also synergistically acts with colistin against colistin-susceptible strain *E. coli* J53 (FICI≤0.141), reducing the MIC from 1 µg/ml to ≤0.016 µg/ml when 10 µg/ml of otilonium bromide is used.

Such a synergistic antimicrobial effect is also observable in other Gram-negative strains on both colistin-susceptible and colistin-resistant Gram-negative pathogens, suggesting that otilonium bromide is a potential broad spectrum colistin adjuvant that can act on all major Gram-negative bacterial pathogens including *Pseudomonas aeruginosa, Acinetobacter baumannii* and *Salmonella Typhimurium*.

TABLE 1

MICs of colistin in colistin-resistant and colistin-susceptible clinical bacterial isolates in the presence of otilonium bromide (Ob)

| Species | ID Gram-negative | Ob MIC (µg/ml) Ob | Colistin MIC (µg/ml) Colistin | Colistin + 10 ug/ml Ob | Colistin + 20 ug/ml Ob |
|---|---|---|---|---|---|
| Colistin-resistant | | | | | |
| E. coli | 2016.2.5 1149-1 | >64 | 8 | 4 | 1 |
| E. coli | WZ3955 | >64 | 8 | 4 | 1 |
| E. coli | X2169 | >64 | 16 | 4 | 2 |
| E. coli | WZ2431 | >64 | 8 | 2 | 0.5 |
| E. coli | WZ3920 | >64 | 4 | 2 | ≤0.25 |
| E. coli | WZ2909 | >64 | 16 | 8 | 1 |
| E. coli | 5 | >64 | 8 | 4 | ≤0.25 |
| E. coli | CX116 | >64 | 2 | ≤0.25 | ≤0.25 |
| E. coli | WZ3903 | >64 | 4 | ≤0.25 | ≤0.25 |
| E. coli | 101 | >64 | 8 | 4 | 1 |
| E. coli | CX48 | >64 | 8 | 4 | 1 |
| E. coli | WZ3906 | >64 | 8 | 4 | 1 |
| E. coli | 812 | >64 | 16 | 4 | 1 |
| E. coli | WZ3951 | >64 | 16 | 8 | 2 |
| E. coli | 12.12.0487 | >64 | 8 | 2 | 0.5 |
| E. coli | 34650 | >64 | 8 | 2 | 0.5 |
| E. coli | CX53 | >64 | 8 | 4 | 2 |
| E. coli | 119 | >64 | 16 | 4 | 2 |
| A. baumannii | ABJZ-45 | 20 | 4 | 0.0625 | — |
| A. baumannii | ABJZ-46 | 20 | 4 | 0.5 | — |
| A. baumannii | ABJZ-50 | 20 | 4 | 0.25 | — |
| A. baumannii | ABJZ-72 | 20 | 4 | 0.125 | — |
| A. baumannii | ATCC17978 | 20 | 4 | 0.125 | — |
| Colistin-susceptible | | | | | |
| S. Typhimurium | PY01 | >64 | 2 | 0.125 | 0.03 |
| E. coli | Bw25113 | >64 | 2 | 0.03 | ≤0.015 |
| P. aeruginosa | PA01 | >64 | 2 | 0.5 | 0.25 |
| P. aeruginosa | PAERC 10.296 | >64 | 2 | 0.0625 | 0.0625 |
| P. aeruginosa | PAERC 11.2309 | >64 | 2 | 0.5 | 2 |
| P. aeruginosa | PAERC 11.236 | >64 | 2 | 0.5 | 0.5 |
| P. aeruginosa | PAERC 11.603 | >64 | 2 | 0.5 | 0.25 |
| P. aeruginosa | PAERC 12.1478 | >64 | 2 | 0.5 | 0.125 |
| P. aeruginosa | PAER 2011-3010 | >64 | 2 | 1 | 0.25 |
| P. aeruginosa | PAER 2011-3252 | >64 | 2 | 0.5 | 0.25 |
| P. aeruginosa | PAER 2012-1527 | >64 | 2 | 2 | 0.5 |

To further evaluate the synergistic antimicrobial effect of otilonium bromide and colistin on colistin-resistant and colistin-susceptible *E. coli*, time-kill curves are constructed for the test strains show that the growth of colistin-resistant *E. coli* could only be inhibited by colistin at 32 µg/ml and higher concentrations. However, the effective bactericidal concentration of colistin could be reduced to 8 µg/ml in the presence of 20 µg/ml of otilonium bromide. For colistin-susceptible *E. coli,* 8 µg/ml of colistin is required to eradicate the strains. However, in the presence of 20 µg/ml of otilonium bromide 1 µg/ml colistin is sufficient to achieve complete eradication of the organism. This suggests that otilonium bromide dramatically enhances the bactericidal activity of colistin against both colistin-resistant and colistin-susceptible *E. coli*. Thus, without intending to be limited by theory, it is believed that this synergistic mechanism is not limited to the inhibition of the colistin resistance mechanism.

The strong synergistic antimicrobial effect exhibited by otilonium bromide and colistin is visualized by performing LIVE/DEAD cell viability assay. Fluorescence microscopy quantifies the number of live and dead cells and determines the degree of reduction in colistin concentration in the drug combination required for effective eradication of the test organism. This test indicates that most or all mcr-1-bearing *E. coli* strains were alive upon treatment with saline, 8 μg/ml of colistin alone or 20 μg/ml of otilonium bromide alone. However, in the presence of 20 μg/ml of otilonium bromide, 4 μg/ml of colistin eradicates >97% of the bacteria.

EXAMPLE 2

Eradication of Clinical Colistin-Resistant *E. coli* in Mouse Infection Model

Figure 2:
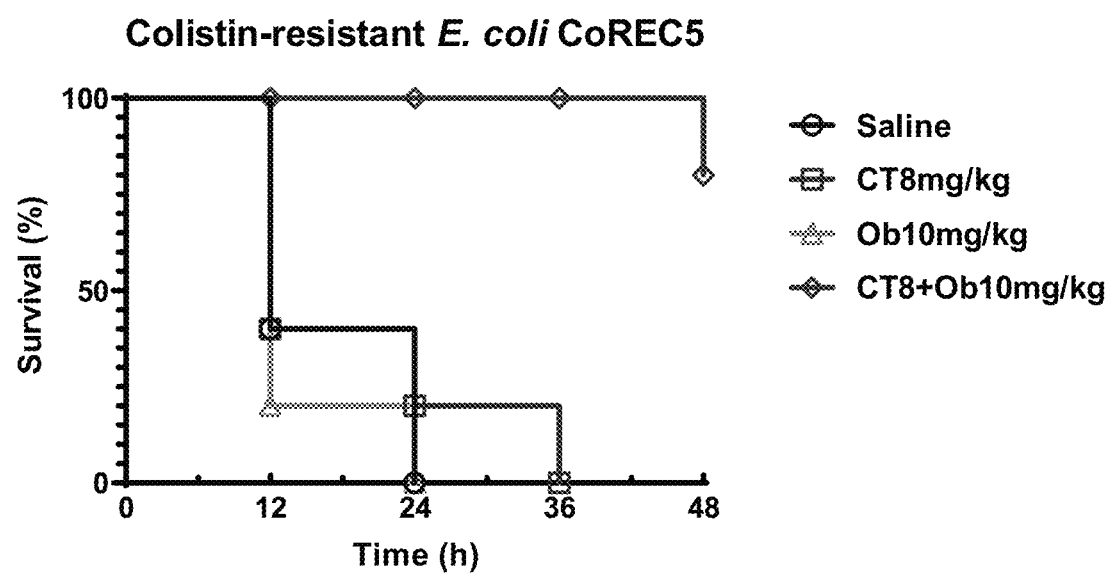
FIG. 2 shows a graph of the in vivo antimicrobial effect of an embodiment of the invention in a mouse infection model.

FIG. 2 shows a graph of the in vivo antimicrobial effect of an embodiment of the invention, specifically the combination otilonium bromide and colistin, in a mouse infection model. The combination of otilonium bromide and colistin is further tested in a mouse sepsis model, showing that otilonium bromide re-sensitizes colistin-resistant CRE (carbapenem-resistance enteroabcteriaceae) to colistin. This experiment is performed in triplicate. The mice are infected intraperitoneally with $6.0 \times 10^8$ CFU *E. coli* CoREC5 by injection.

The mice are subsequently injected intraperitoneally with 8 mg/kg of colistin, 10 mg/kg of Ob and a combination of both. The treatment is administrated every 12 hours for 48 hours. Colistin is in the form of colistin sulfate salt.

All mice treated with saline, monotreatment with colistin (CT, 8 mg/kg)), and monotreatment with otilonium bromide (Ob, 10 mg/kg) died within 36 h upon treatment. However, 80% of the animals survived treatment with the combination of otilonium bromide (10 mg/kg) and colistin (8 mg/kg) at 48 hpi (hours post injection). Accordingly, it is believed that the invention exhibits synergistic antimicrobial effect in vivo as well as in vitro. Furthermore, it is believed that the efficacy of the mouse animal model is a reliable proxy and reasonable predictor for likely efficacy in humans.

EXAMPLE 3

Eradication of Tolerant Gram-Negative Bacterial Cells In Vitro

Starvation-induced bacterial sub-population tolerant cells of colistin-resistant and colistin-susceptible *E. coli* and *A. baumannii* strains are tested against the bactericidal effect of the combination of otilonium bromide and colistin. Otilonium bromide is found to strongly enhance the colistin efficacy. Compared to the initial population size of $\sim 10^8$ CFU/mL of mcr-1-bearing *E. coli* strain re-suspended in saline, the size of the viable population remained at a high level of $5*10^5$ CFU/ml upon treatment with colistin (32 μg/ml) for 24 hours. However, after treatment with the combination of pre-mixed 10 μg/ml of otilonium bromide and 2 μg/ml of colistin, the entire drug tolerant population was effectively eradicated within 24-hours. The incubation temperature is 37° C. Ob and colistin are added at the same time. Thus, it is believed that data shows otilonium bromide may also act synergistically with colistin on the tolerant sub-population of colistin-susceptible *E. coli* and *A. baumannii* strains by reducing the concentration of colistin required to completely eradicate such sub-population to 1 μg/ml in a 24-hour treatment. These data further reinforces the belief that otilonium bromide has high potential to be developed into an adjuvant and/or a therapeutic agent in a drug composition and method/use for eradication of bacterial tolerant sub-populations, especially of *E. coli* and *A. baumannii*.

EXAMPLE 4

Eradication of Tolerant Gram-Negative Bacterial Cells In Vitro

All bacterial populations, including those of non-antibiotic resistant strains, are known to harbor drug tolerant sub-population that do not respond to antimicrobial actions of antibiotics. We tested the bactericidal effect of the otilonium bromide and colistin combination on antibiotic tolerant bacterial sib-population. otilonium bromide was found to strongly enhance the efficacy of colistin in killing the starvation-induced bacterial tolerant cells of colistin-resistant and colistin-susceptible *E. coli* J53 and *A. baumannii* 17978 strains. Compared to the initial population size of $\sim 10^8$ CFU/mL of mcr-1-bearing *E. coli* strain re-suspended in saline, the size of the viable population remained at a high level of $5*10^5$ CFU/ml upon treatment with colistin at 32 μg/ml for 24 hours. However, the entire drug tolerant population was effectively eradicated by 2 μg/ml of colistin in the presence of 20 μg/ml of otilonium bromide in 24-hour treatment. otilonium bromide could also act synergistically with colistin on the tolerant sub-population of colistin-susceptible *E. coli* and *A. baumannii* strains by reducing the concentration of colistin required to completely eradicate such sub-population to 1 μg/ml in a 24-hour treatment. This data suggests that otilonium bromide has high potential to be developed into a therapeutic agent for the eradication of tolerant bacterial sub-populations.

EXAMPLE 5

Otilonium Bromide Enhances the Ability of Colistin to Cause Membrane Disruption

It is believed that colistin exhibits high bactericidal efficacy against Gram-negative pathogens through specifically binding to the negatively-charged phosphate group of lipid A in lipopolysaccharides (LPSs) in the cell membrane of Gram negative bacteria. This in turn causes an increase in cell membrane permeability and leakage of cellular contents resulting in cell death (see, Ahmed, et al., Colistin and its role in the Era of antibiotic resistance: an extended review (2000-2019), *Emerging Microbes & Infections* vol. 9, pp. 868-85, 2020). The mechanism of colistin resistance in Gram-negative bacteria mainly involves modification of lipid A, which renders colistin binding ineffective (see, Poirel, et al., Polymyxins: antibacterial activity, susceptibility testing, and resistance mechanisms encoded by plasmids or chromosomes, *Clin. Microbiol. Rev.*, vol. 30, pp. 557-96, 2017). From the experimental data herein, it is hypothesized that otilonium bromide may restore the ability of colistin (and similar-mechanism drug actives) to disrupt the bacterial cell membrane.

Figure 3:
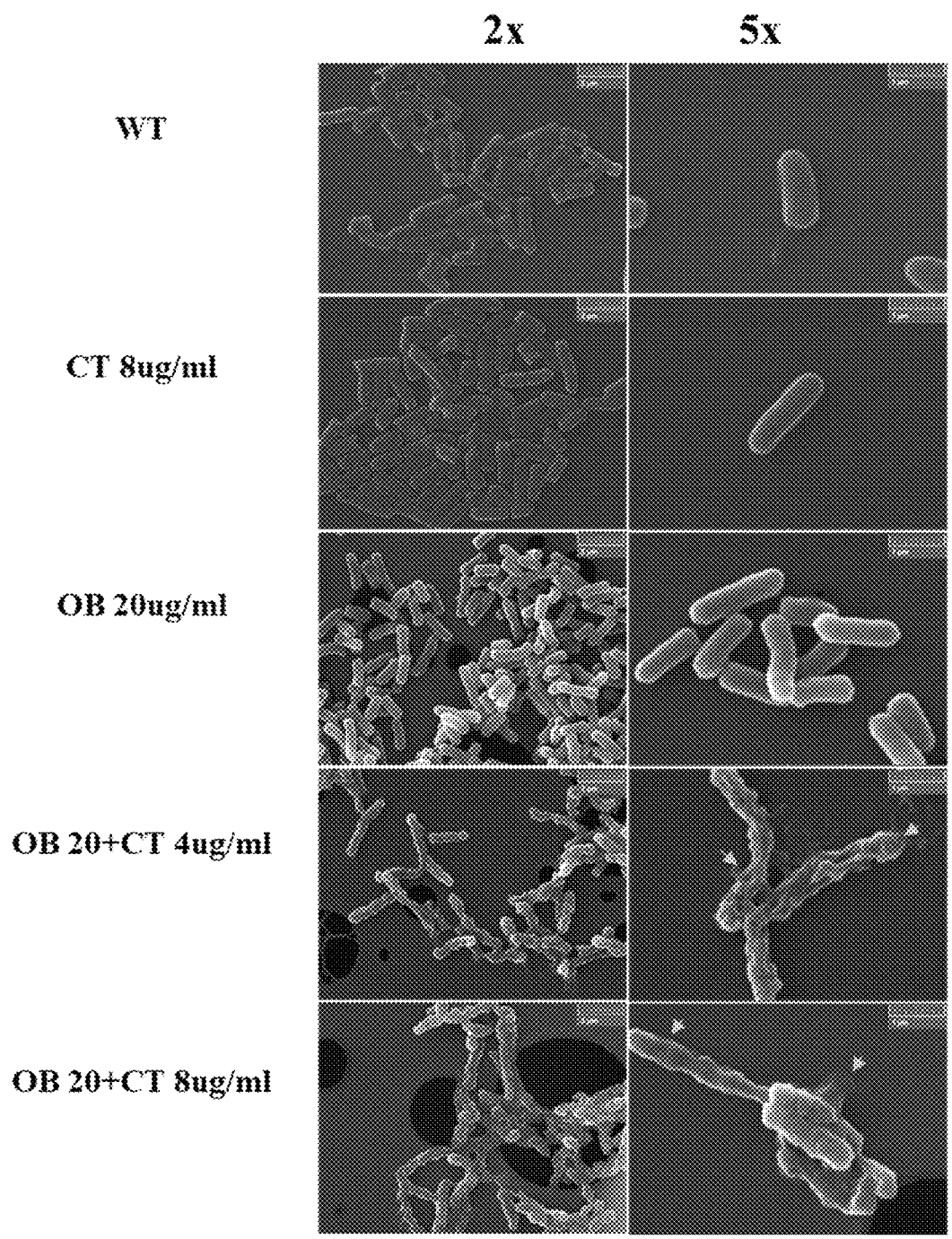
FIG. 3 shows scanning electronic microscopy images of mcr-1-bearing *E. coli* J53 as wild type (\VT) and treated with colistin (CT) alone, otilonium bromide (Ob) alone, and various embodiments of the invention herein.

To test this hypothesis, FIG. 3 shows scanning electronic microscopy of mcr-1-bearing *E. coli* J53 as wild type (WT) and treated with colistin (CT) alone, otilonium bromide (Ob) alone, and various embodiments of the invention herein (e.g., combinations of CT and Ob). SEM visualizes the morphological changes in colistin-resistant *E. coli* upon treatment with sub-MIC colistin (8 µg/ml), otilonium bromide (20 µg/ml) and the combination of both. No morphological changes were observed when mcr-1-bearing *E. coli* was treated with sub-MIC of otilonium bromide or colistin. When treated with 4 µg/ml of colistin+20 µg/ml of otilonium bromide, one easily observes that the bacterial envelope is completely disrupted, the cytosol leaks, and the cell membrane shrinks. Treatment with 20 µg/ml otilonium bromide+8 µg/ml of colistin resulted in more severe cell membrane disruption, suggesting that the presence of otilonium bromide may restore the killing effect of colistin on colistin-resistant *E. coli*.

SYTOX™ Green (available from ThermoFisher Scientific) staining analysis assesses the membrane permeability of colistin-resistant *E. coli* before and after treatment with the colistin and otilonium bromide combination. SYTOX Green is a green-fluorescent nucleotide dye used to test membrane permeability and membrane integrity. Green fluorescence is detected by fluorescence spectrometer when bacterial cell integrity is destroyed and membrane permeability increases. Consistently, the data shows that individually, otilonium bromide and colistin each cause a significant increase in fluorescence in mcr-1-bearing *E. coli*, indicating that both drugs could cause increases in bacterial cell membrane permeability.

Figure 4A:
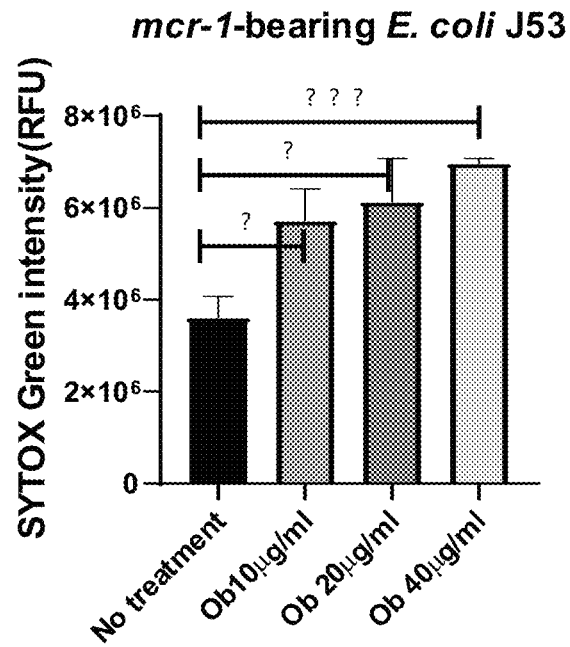
FIG. 4a shows a graph of SOYTOX™ Green intensity for mcr-1-bearing *E. coli* J53 treated with otilonium bromide.
Figure 4B:
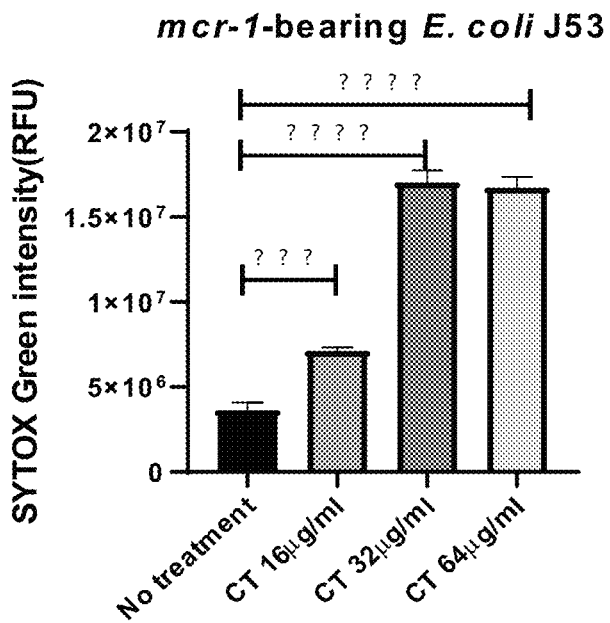
FIG. 4b shows a graph of SOYTOX™ Green intensity for mcr-1-bearing *E. coli* J53 treated with colistin.

FIG. 4a shows a graph of SOYTOX™ Green intensity for mcr-1-bearing *E. coli* J53 treated with otilonium bromide, while FIG. 4b shows a graph of SOYTOX™ Green intensity for mcr-1-bearing *E. coli* J53 treated with colistin. The data shows that by itself, otilonium bromide's ability to enhance membrane permeability is significantly lower than colistin. As expected, treatment with the otilonium bromide and colistin combination caused a drastic increase in membrane permeability, suggesting that the effective bactericidal concentration of colistin can be reduced in the presence of otilonium bromide.

Figure 4C:
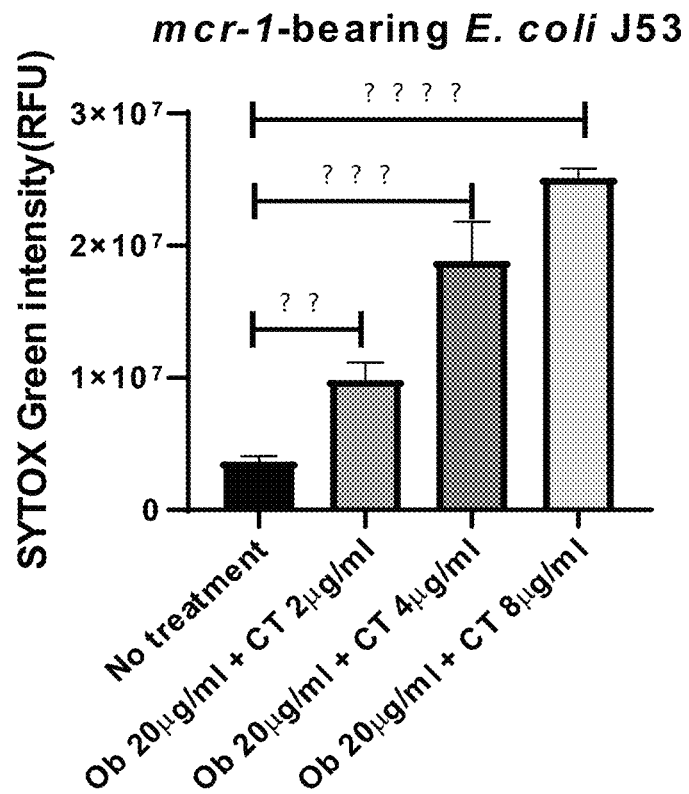
FIG. 4c shows a graph of SOYTOX™ Green intensity for mcr-1-bearing *E. coli* J53 treated with embodiments of the present invention.

Furthermore, FIG. 4c shows a graph of SOYTOX™ Green intensity for mcr-1-bearing *E. coli* J53 treated with embodiments of the present invention. FIG. 4c depicts a significant fluorescence increase when mcr-1-bearing *E. coli* J53 is treated with a combination of 20 µg/ml otilonium bromide and 8 µg/ml colistin, when compared to either monotreatment with colistin or otilonium bromide at the same concentration (cf. FIG. 4a and FIG. 4b).

It is known that previous studies demonstrated that electrostatic interaction between colistin and the negatively charged LPS causes displacement of divalent ions ($Ca^{2+}$ and $Mg^{2+}$) from the phospholipids and hence disruption of the bacterial cell membrane. It is believed that divalent ions act as a cross-linker promoting the networking of LPS molecules, enhancing the membrane's structural stability, allowing tight LPS packing, and enhancing selective membrane permeability.

Figure 5A:
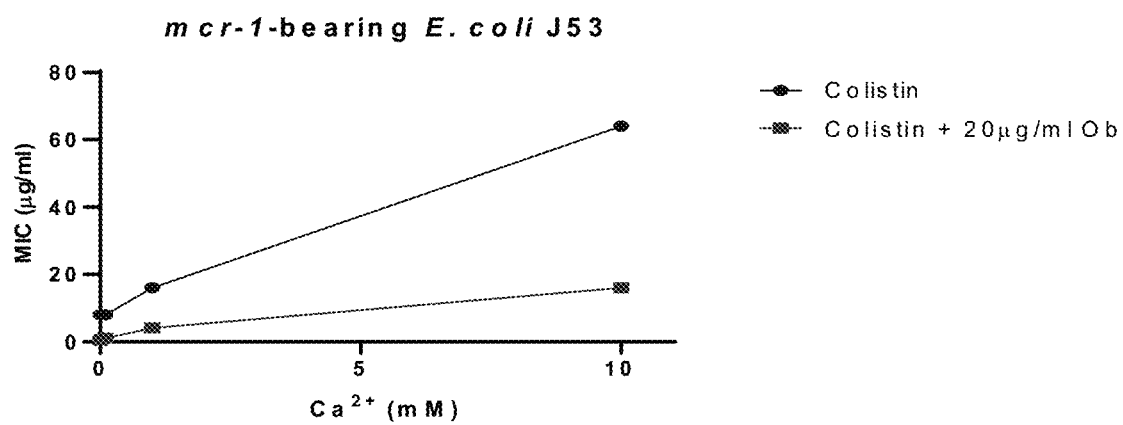
FIG. 5a shows a graph of the $Ca^{2+}$ MIC-dependency of mcr-1-bearing *E. coli* J53.
Figure 5B:
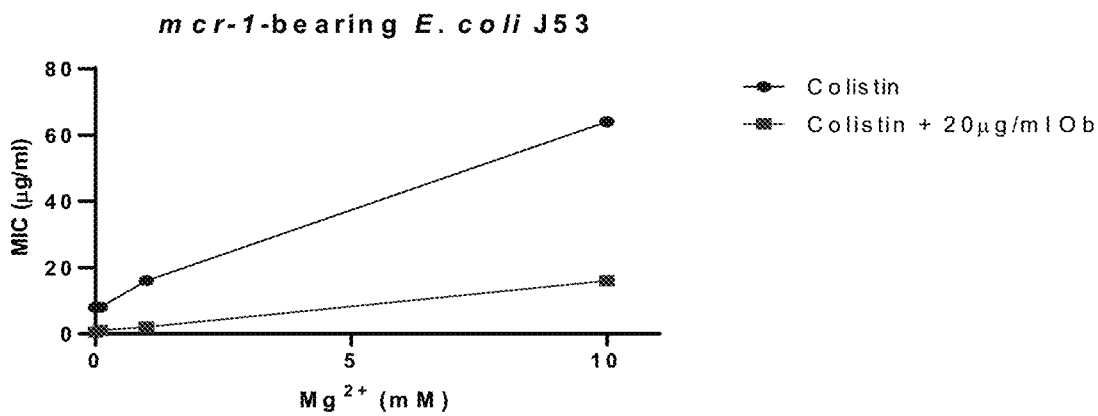
FIG. 5b shows a graph of the $Mg^{2+}$ MIC-dependency of mcr-1-bearing *E. coli* J53.

Accordingly, the effect of divalent ions on the antibacterial activity of otilonium bromide and colistin is investigated. It is theorized that the addition of $Mg^{2+}$ and $Ca^{2+}$, particularly $Ca^{2+}$, could suppress the activity of both colistin and the otilonium bromide and colistin combination on both colistin-resistant and susceptible *E. coli*. FIG. 5a shows a graph of the $Ca^{2+}$ MIC-dependency of colistin vs. an embodiment of the present invention in mcr-1-bearing *E. coli* J53. FIG. 5b shows a graph of the $Mg^{2+}$ MIC-dependency of colistin vs. an embodiment of the present invention in mcr-1-bearing *E. coli* J53. For FIGS. 5a-5b, *E. coli* J53 expressing MCR-1 is treated with colistin and colistin+Ob as indicated in Mueller Hinton II Broth (MHB) that is cation-adjusted; i.e., supplemented with different concentrations of $Mg^{2+}$ and $Ca^{2+}$ ions). The incubation is conducted at 37° C. for 16 hours.

Figure 5C:
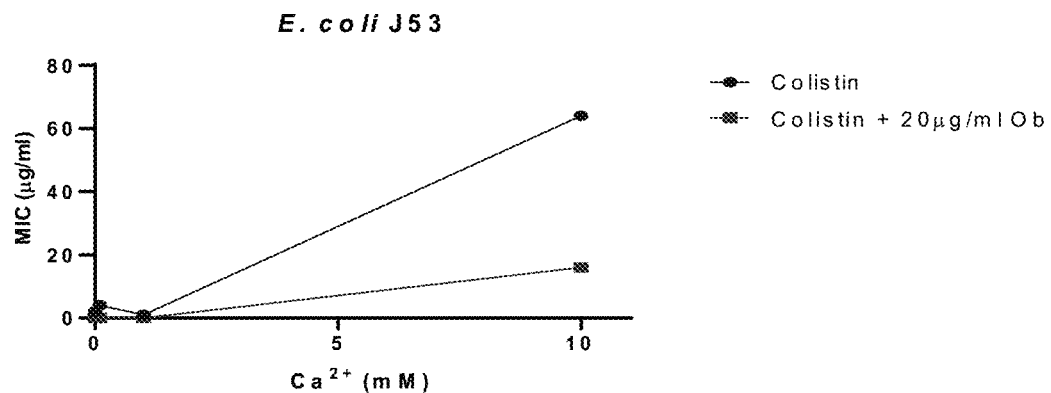
FIG. 5c shows a graph of the $Ca^{2+}$ MIC-dependency of *E. coli* J53.
Figure 5D:
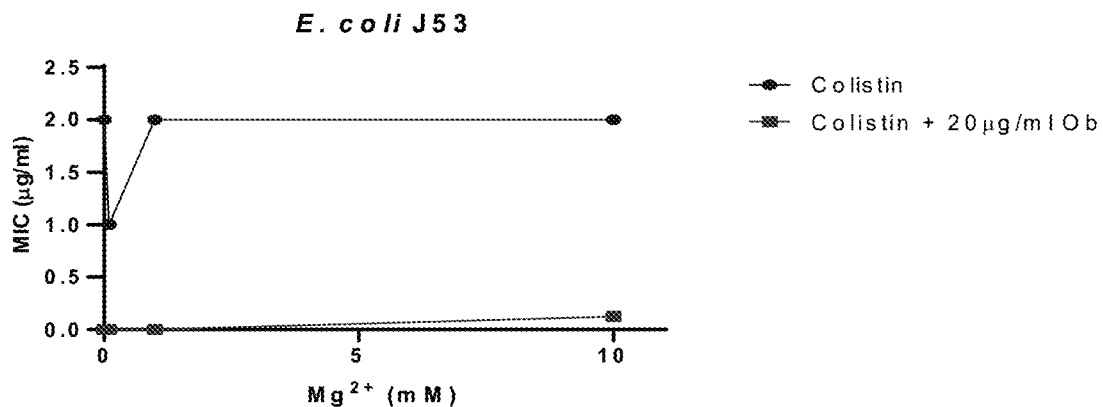
FIG. 5d shows a graph of the $Mg^{2+}$ MIC-dependency of *E. coli* J53.

FIG. 5c shows a graph of the $Ca^{2+}$ MIC-dependency of colistin vs. an embodiment of the present invention in *E. coli* J53. FIG. 5d shows a graph of the $Mg^{2+}$ MIC-dependency of colistin vs. an embodiment of the present invention in *E. coli* J53. For FIGS. 5c-5d, colistin-susceptible *E. coli* J53 is treated with colistin and colistin+Ob as indicated in MHB supplemented with different concentrations of $Mg^{2+}$ and $Ca^{2+}$ ions. The incubation is conducted at 37° C. for 16 hours.

Figure 5E:
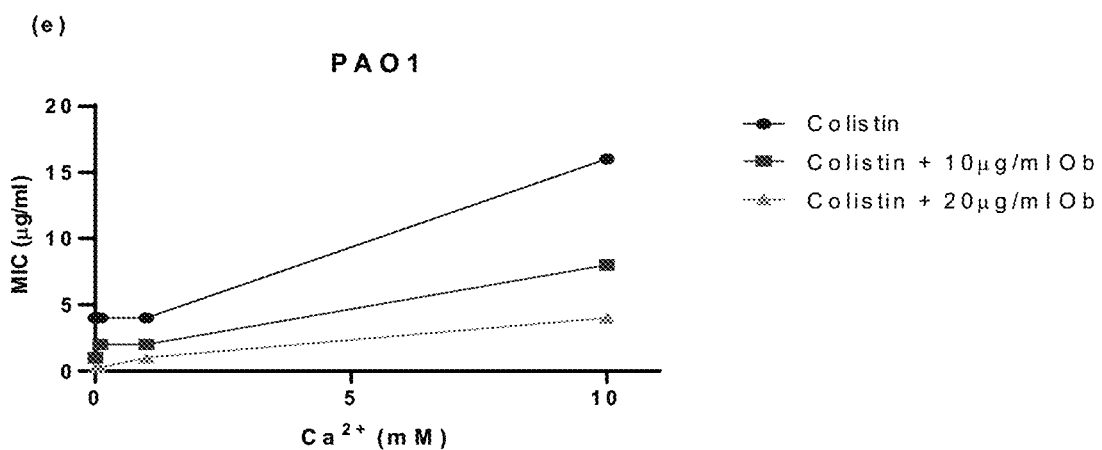
FIG. 5e shows a graph of the $Ca^{2+}$ MIC-dependency of *P aeruginosa* PAO1.
Figure 5F:
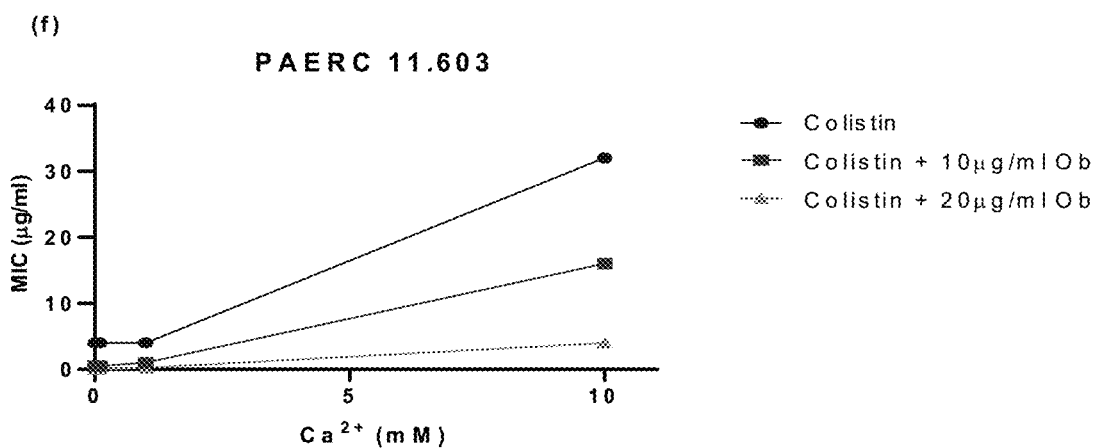
FIG. 5f shows a graph of the $Mg^{2+}$ MIC-dependency of *P. aeruginosa* PAERC 11.603.

FIG. 5e shows a graph of the $Ca^{2+}$ MIC-dependency of colistin vs. an embodiment of the present invention in *P. aeruginosa* PAO1. FIG. 5f shows a graph of the $Mg^{2+}$ MIC-dependency of colistin vs. an embodiment of the present invention in *P. aeruginosa* PAERC 11.603. In FIGS. 5e and 5f, colistin MICs of *P. aeruginosa* PAO1 and PAERC 11.603, respectively, are determined in MHB supplemented with different $Ca^{2+}$ ion concentrations.

In all cases, FIGS. 5a-5f show that supplemented $CA^{2+}$ $^{and}$ $^{Mg}2+$ increase the MIC and thus inhibits the antibiotic effect of colistin and the present invention against mcr-1-bearing *E. coli* J53, *E. coli* J53, and *P. aeruginosa*. Accordingly, it is believed that the addition of a chelant; or a chelant for divalent ions; or a divalent cation chelant, may further improve the activity of the drug formulation, method of use/treatment, disinfection composition, etc. of the present invention.

EXAMPLE 6

Otilonium Bromide Acts as a Membrane Proton Motive Force (PMF) Dissipater

Figure 6A:
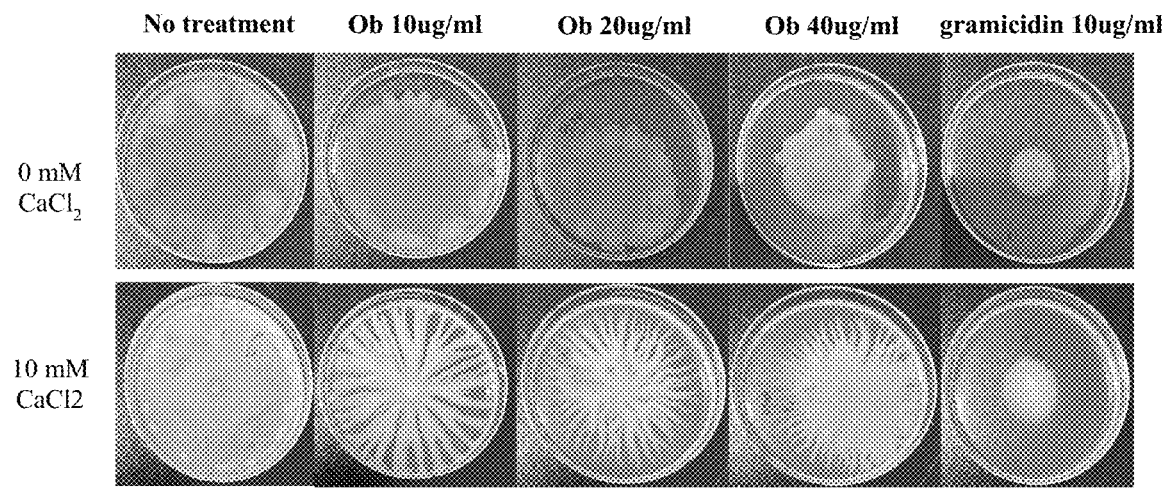
FIG. 6a shows photos of the suppression effect of otilonium bromide compared to gramicidin with *P. aeruginosa* PAO1, with and without $CaCl_2$.

It is believed that flagellar formation and flagellar motor rotation are driven by PMF. To study the effect of otilonium bromide on bacterial motility, *P. aeruginosa*, whose motility on a semisolid surface is dependent upon a functional flagellum, is reviewed. The migration distance of *P. aeruginosa* PAO1 inoculated onto a semisolid agar plates containing otilonium bromide is found to decrease in a dose-dependent manner after overnight incubation. Gramicidin, an ionophore known for acting as PMF dissipater, is the positive control. *P. aeruginosa* PAO1 treated with 40 µM otilonium bromide supplemented with 10 mM calcium ions shows a significant increase in migration distance, again suggesting that 10 mM calcium ions effectively suppresses the inhibitory effect of otilonium bromide on bacterial swarming. FIG. 6a shows photos of the suppression effect of otilonium bromide compared to gramicidin with *P. aeruginosa* PAO1, with and without $CaCl_2$. For the experiments in FIG. 6a, *P. aeruginosa* is inoculated in the center of the semisolid agar containing otilonium bromide at the indicated concentrations, with gramicidin as the positive control. A set of 10 mM $CaCl_2$ and no $CaC_2$ plates are also prepared as indicated.

Figure 6B:
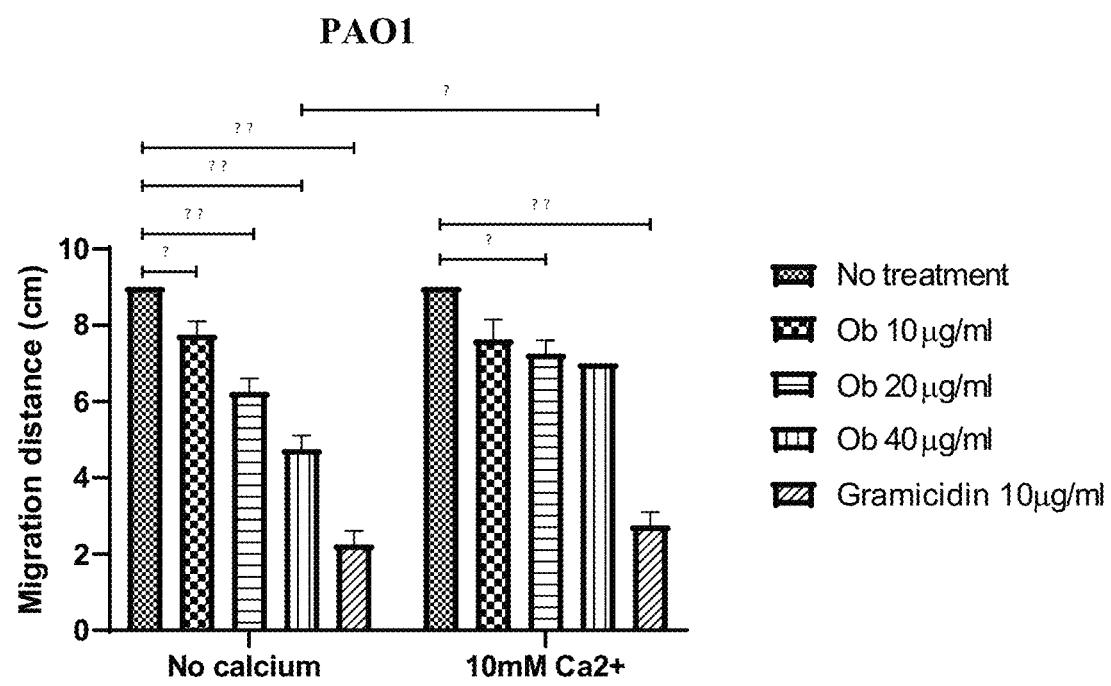

FIG. 6b shows a graph of the migration distance in FIG. 6a. The migration distance is measured in cm and recorded after the inoculated plates ae incubated. The error bars represent the means and standard deviations (SDs). Statistical analysis is performed using unpaired two-tailed student t-test. .*, p<0.05, , p<0.005, *p<0.0005, ****p<0.00005.

Figure 7:
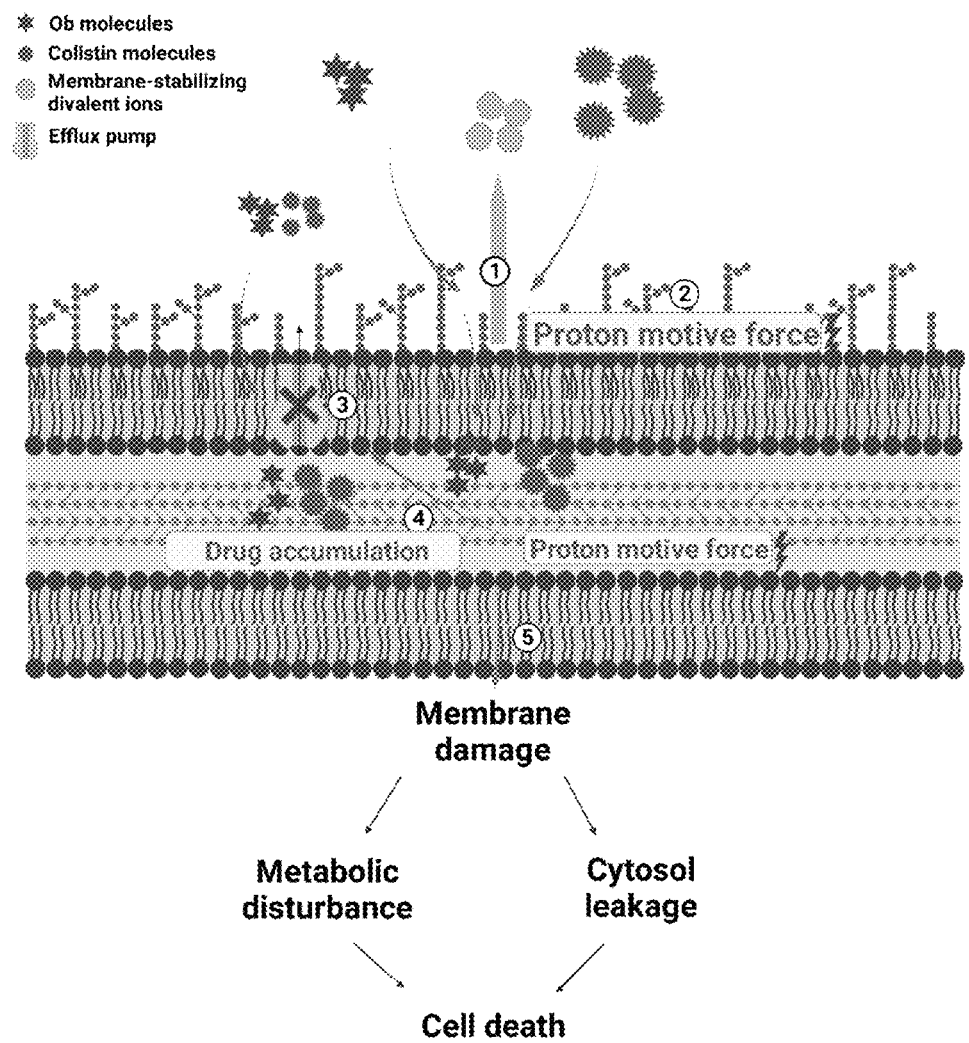
FIG. 7 shows a schematic mechanistic diagram of the of synergic antimicrobial effects of the invention.

FIG. 7 shows a schematic mechanistic diagram of the of synergic antimicrobial effects of an embodiment of the invention herein, such as otilonium bromide and colistin, on colistin-resistant *E. coli*. Without intending to be limited by theory, it is believed that otilonium bromide acts synergistically with colistin to enhance membrane permeabilization by displacement of membrane-stabilizing divalent ions ①  as described herein. The combination of Ob and colistin dissipates the membrane's PMF ② and inhibits drug efflux ③, resulting in the accumulation of the two adjuvant and the drug active. Dissipation of PMF also helps to inhibit the activity of the efflux pump ④. The collapse of PMF and selective membrane permeability causes a cascade of membrane damage, further leading to uncontrollable cytosol leakage and eventually cell death ⑤.

It should be understood that the above only illustrates and describes examples whereby the present invention may be carried out, and that modifications and/or alterations may be made thereto without departing from the spirit of the invention.

It should also be understood that certain features of the invention, which are, for clarity, described in the context of separate embodiments, may also be provided in combination in a single embodiment. Conversely, various features of the invention which are, for brevity, described in the context of a single embodiment, may also be provided separately, or in any suitable subcombination.

All references specifically cited herein are hereby incorporated by reference in their entireties. However, the citation or incorporation of such a reference is not necessarily an admission as to its appropriateness, citability, and/or availability as prior art to/against the present invention.

What is claimed is:

1. An adjuvant for a drug active comprising an effective amount of otilonium bromide, and wherein the drug active is selected from the group consisting of colistin, colistimethate sodium, colistin sulfate, polymyxin B, and a combination thereof.

* * * * *